United States Patent
Slater

(10) Patent No.: US 7,859,660 B2
(45) Date of Patent: Dec. 28, 2010

(54) LASER INDICATION LIGHT CONFIGURATION

(75) Inventor: Joseph B. Slater, Dexter, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 1686 days.

(21) Appl. No.: 10/101,798

(22) Filed: Mar. 19, 2002

(65) Prior Publication Data

US 2002/0141460 A1 Oct. 3, 2002

Related U.S. Application Data

(60) Provisional application No. 60/277,192, filed on Mar. 20, 2001.

(51) Int. Cl.
*G01J 3/44* (2006.01)
*G01J 3/00* (2006.01)
*G02C 7/10* (2006.01)

(52) U.S. Cl. .................... 356/301; 356/300; 351/41
(58) Field of Classification Search ............... 2/6.3, 2/426–454; 356/300–301; 351/41
See application file for complete search history.

(56) References Cited

U.S. PATENT DOCUMENTS

| | | | | |
|---|---|---|---|---|
| 4,453,806 A | * | 6/1984 | Wick | 359/707 |
| 4,595,262 A | * | 6/1986 | Ogle | 359/409 |
| 4,744,663 A | * | 5/1988 | Hamashima et al. | 356/615 |
| 4,917,486 A | * | 4/1990 | Raven et al. | 351/221 |
| 4,968,148 A | * | 11/1990 | Chow et al. | 356/427 |
| 5,281,211 A | * | 1/1994 | Parel et al. | 606/5 |
| 5,325,227 A | * | 6/1994 | Templeton et al. | 359/241 |
| 5,389,788 A | * | 2/1995 | Grinberg et al. | 250/331 |
| 5,729,381 A | * | 3/1998 | Havens et al. | 359/361 |
| 5,748,655 A | * | 5/1998 | Yessik et al. | 372/22 |
| 5,751,416 A | * | 5/1998 | Singh et al. | 356/311 |
| 5,943,128 A | * | 8/1999 | Slater | 356/301 |
| 6,038,363 A | * | 3/2000 | Slater et al. | 385/147 |
| 6,066,129 A | * | 5/2000 | Larson | 606/10 |

(Continued)

OTHER PUBLICATIONS

California Institute of Technology, Laser Safety Manual, Jan. 1998, pp. 1-5.

*Primary Examiner*—Minsun Harvey
*Assistant Examiner*—Phillip Nguyen
(74) *Attorney, Agent, or Firm*—Gifford, Krass, Sprinkle, Anderson & Citkowski, P.C.

(57) ABSTRACT

Indicator light apparatus and methods associated with a laser beam having a primary wavelength enable an operator to see the indicator while wearing protective eyewear tuned to the primary wavelength. The apparatus includes a source of indicator light other than the primary wavelength, a first optical element for co-injecting the indicator light into the laser beam to form a co-propagating beam, and an optical or physical configuration enabling an operator to view light from the co-propagating beam. The first optical element may be some form of beam splitter or combiner, and the configuration enabling an operator to view light from the co-propagating beam uses a diffuser upon which the co-propagating beam impinges. The indicator light is preferably derived from an inexpensive source, such as a diode laser operating in the 670-690 nm range. The invention is useful in many different environments, including stimulate emission systems, wherein one or more optical elements are used to direct the laser beam onto a sample to stimulate an optical emission therefrom. The stimulated emission may be representative of a Raman or fluorescence spectrum, for example.

4 Claims, 1 Drawing Sheet

U.S. PATENT DOCUMENTS

| | | | |
|---|---|---|---|
| 6,128,123 A * | 10/2000 | Wagner | 359/260 |
| 6,168,278 B1 * | 1/2001 | Mukai | 359/612 |
| 6,210,399 B1 * | 4/2001 | Parel et al. | 606/5 |
| 6,243,219 B1 * | 6/2001 | Hutcheson et al. | 359/885 |
| 6,259,517 B1 * | 7/2001 | Tedesco et al. | 356/73.1 |
| 6,315,412 B1 * | 11/2001 | Snodderly et al. | 351/200 |
| 6,351,306 B1 * | 2/2002 | Tedesco et al. | 356/301 |
| 6,384,982 B1 * | 5/2002 | Spitzer | 359/630 |
| 6,401,589 B1 * | 6/2002 | Pinkus et al. | 89/1.1 |

\* cited by examiner

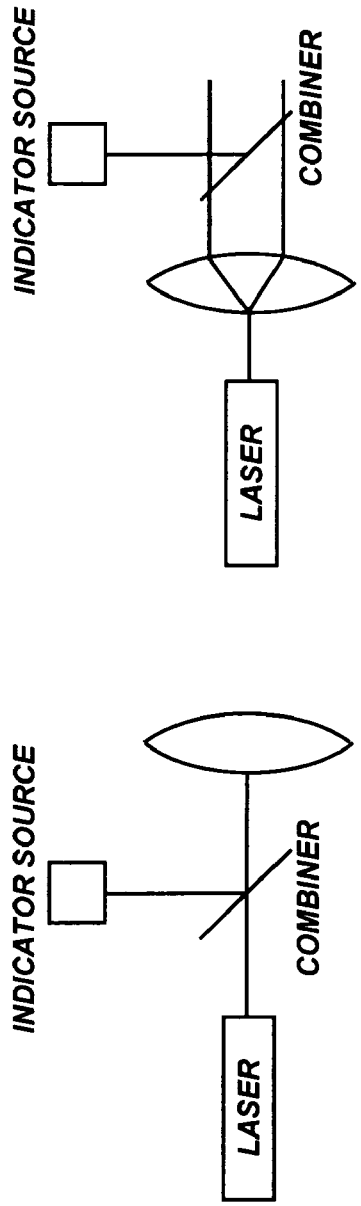
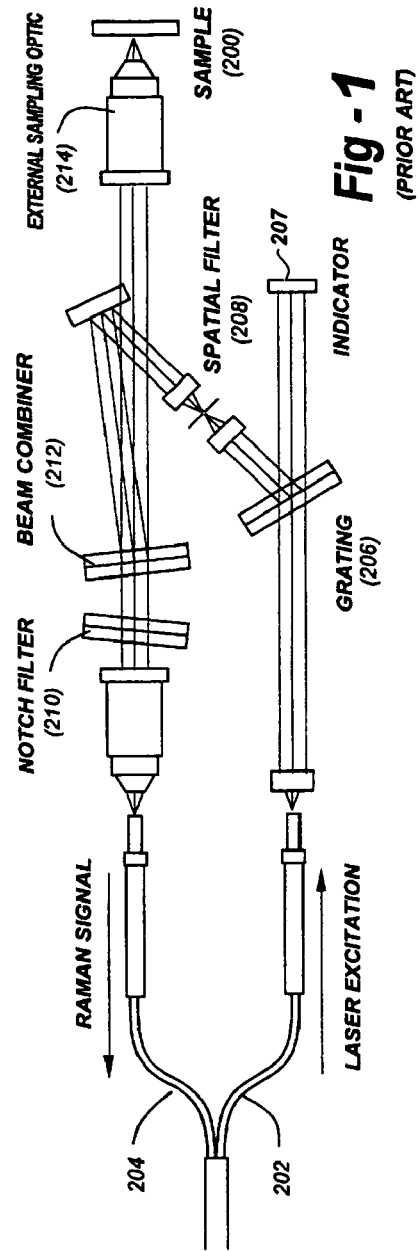

LASER INDICATION LIGHT CONFIGURATION

REFERENCE TO RELATED APPLICATION

This application claims priority from U.S. provisional patent application Ser. No. 60/277,192, filed Mar. 20, 2001, the entire contents of which being incorporated herein.

FIELD OF THE INVENTION

This invention relates generally to laser safety and, in particular, to apparatus and methods for co-injecting indicator light at a wavelength different from that of a primary laser into the path of the laser beam, thereby enabling an operator to see the indicator light even wearing protective eyewear tuned to the primary laser radiation.

BACKGROUND OF THE INVENTION

There is currently a rule in the industry that laser equipment supplied with an indicator lamp use a wavelength other than that of the laser, so that an operator wearing protective eyewear will be able to see the indicator lamp when the laser is on. As a consequence, previous arrangements wherein a small portion of the laser light itself is leaked out for indicator purposes are no longer acceptable.

Candidate systems include optical stimulated-emission arrangements wherein laser light is used to illuminate a sample under investigation. The prior-art system of FIG. 1 shows the delivery of an excitation laser beam to a sample under test 200 by way of an excitation fiber-optic cable 202. Scattered light from the sample is collected by the probe head and routed back to the analyzer via a separate collection fiber-optic cable 204. The non-shifted or Rayleigh line is removed from the collected scatter by a notch filter 210 supported in the collection path, and a beam combiner 212 serves to combine the laser beam delivery path onto a common optical axis with the collection path, so that a common sampling optic 214 may be used for both paths.

In this particular configuration, a grating 206 and spatial filter 208 are inserted into the beam delivery path to remove the scattering signature of the fiber itself. Conveniently, since some of the excitation leaks through the grating 206, this stray radiation may be used as an indicator, in this case by striking diffuser 207 mounted on the probe head enclosure. However, as explained above, since this indicator light is identical to that of the primary beam, use of modem, efficient laser protection eyewear will prevent an operator from knowing whether the laser has been switched on. There is an outstanding need for solution to this problem, preferably an inexpensive solution involving a wavelength other than that of the laser to reliably indicate the present/absence of a laser beam which might otherwise be harmful to an operator unless protective eyewear is used.

SUMMARY OF THE INVENTION

Broadly, this invention resides in indicator light apparatus and methods associated with a laser beam having a primary wavelength, enabling an operator to see the indicator while wearing protective eyewear tuned to the primary wavelength. In terms of apparatus, the arrangement includes a source of indicator light other than the primary wavelength, a first optical element for co-injecting the indicator light into the laser beam to form a co-propagating beam; and an optical or physical configuration enabling an operator to view light from the co-propagating beam.

In the preferred embodiment, the first optical element is some form of beam splitter or combiner, and the configuration enabling an operator to view light from the co-propagating beam uses a diffuser upon which the co-propagating beam impinges. The indicator light is preferably derived from an inexpensive source, such as a diode laser operating in the 670-690 nm range. The invention is useful in many different environments, including stimulate emission systems, wherein one or more optical elements are used to direct the laser beam onto a sample to stimulate an optical emission therefrom. The stimulated emission may be representative of a Raman or fluorescence spectrum, for example.

BRIEF DESCRIPTION OF THE DRAWINGS

FIG. 1 is block diagram of a fiber-optic sample probe wherein a portion of the laser excitation is used as an indicator light;

FIG. 2A shows how light of a non-laser wavelength may be co-injected into a non-collimated laser beam; and FIG. 2B shows how light of a non-laser wavelength may be co-injected into a collimated laser beam.

DETAILED DESCRIPTION OF THE INVENTION

Broadly, this invention co-injects indicator light at a wavelength different from that of the primary laser into the path of the beam, such that if a leak path is used, the light will include a wavelength which is different from that of the laser, enabling an operator to see the light even wearing protective eyewear tuned to the primary laser radiation. The indicator light may be merged into the primary beam at any convenient location, including immediately in front of the source. Various optical components may be used to perform the merging function, including dichroic beam splitters/combiners, course WDM devices, and so forth, and the beam combining may take place in a non-collimated (FIG. 2A) or collimated space (FIG. 2B).

A distinct advantage of the invention is that existing systems such as that depicted in FIG. 1 which use a leak path from the primary laser need not be modified other than the addition of the inexpensive non-primary source. In terms of the indicator light source, an inexpensive diode laser of the type used for laser pointers, and the like, may be used, such as a compound semiconductor device operating in the 670-690 nm range, though other wavelengths are certainly possible. Preferably the indicator light would be electrically interconnected so that it is switched on and off in unison with the primary laser source.

Depending upon the application, the wavelength of the indicator light would be chosen so as not to interfere with system operation. For example, in a stimulated emission/detection system, the wavelength of the indicator light would be selected so as not to be detrimental if it reached a sample under investigation, or fall within the detection space used for analysis, as might be the case with a Raman or fluorescent system. In such a situation, a wavelength of, say, 690 nm would be useful, since this falls outside of Raman systems based upon 532 or 785 nm excitation.

I claim:

1. Indicator light apparatus for an optical stimulated-emission system including a laser beam having a primary wavelength and operator-worn protective eyewear tuned to reject the primary wavelength, the apparatus comprising:

one or more focusing optical elements for directing the laser beam onto a sample to stimulate a Raman or fluorescence spectrum therefrom;

one or more collection optical elements to collect the Raman or fluorescence spectrum;

a source of indicator light other than the primary wavelength;

a first optical element for co-injecting the indicator light into the laser beam to form a co-propagating beam; and an optical configuration enabling an operator to view the co-propagating beam and detect the presence of the indicator light while wearing the protective eyewear.

2. The indicator light apparatus of claim 1, wherein the first optical element is a beam combiner.

3. The indicator light apparatus of claim 1, wherein the configuration enabling an operator to view light from the co-propagating beam includes a diffuser upon which the co-propagating beam impinges.

4. The indicator light apparatus of claim 1, wherein the indicator light is in the 670 - 690 nm range.

* * * * *